United States Patent [19]

Proxmire

[11] Patent Number: 4,936,840
[45] Date of Patent: Jun. 26, 1990

[54] METHOD OF REDUCING FASTENER IRRITATION AND WAIST DROOP IN A DISPOSABLE DIAPER

[75] Inventor: Deborah L. Proxmire, Larsen, Wis.

[73] Assignee: Kimberly-Clark Corporation, Neenah, Wis.

[21] Appl. No.: 140,000

[22] Filed: Dec. 31, 1987

[51] Int. Cl.$^5$ ............................................. A61F 13/16
[52] U.S. Cl. ................................ 604/385.2; 601/391; 601/397
[58] Field of Search ................. 604/385.1, 385.2, 386, 604/387, 389, 390, 391, 392, 393, 394, 395, 396, 397, 398, 399, 400, 401, 402, 350, 364, 370

[56] References Cited

U.S. PATENT DOCUMENTS

| | | | |
|---|---|---|---|
| 2,141,105 | 12/1938 | Eller et al. | 128/284 |
| 2,936,758 | 5/1960 | Csulits | 128/284 |
| 3,196,874 | 7/1965 | Hrubecky | 128/287 |
| 3,370,590 | 2/1968 | Hokanson et al. | 128/290 |
| 3,509,881 | 5/1970 | Sabee | 128/287 |
| 3,599,640 | 8/1971 | Larson | 128/286 |
| 3,644,157 | 2/1972 | Draper | 156/160 |
| 3,653,381 | 4/1972 | Warnken | 128/284 |
| 3,658,064 | 4/1972 | Pociluyko | 128/287 |
| 3,860,003 | 1/1975 | Buell | 128/287 |
| 3,882,871 | 5/1975 | Taniguchi | 128/287 |
| 4,022,210 | 5/1977 | Glassman | 128/284 |
| 4,036,233 | 7/1977 | Kozak | 128/287 |
| 4,050,462 | 9/1977 | Woon et al. | 128/287 |
| 4,166,464 | 9/1979 | Korpman | 128/287 |
| 4,205,679 | 6/1980 | Repke et al. | 128/287 |
| 4,324,245 | 4/1982 | Mesek et al. | 128/287 |
| 4,338,939 | 7/1982 | Daville | 128/286 |
| 4,355,425 | 10/1982 | Jones et al. | 2/402 |
| 4,397,646 | 8/1983 | Daniels et al. | 604/381 |
| 4,425,128 | 8/1984 | Motomura | 604/381 |
| 4,500,316 | 2/1985 | Damico | 604/385.1 |
| 4,516,975 | 5/1985 | Mitchell | 604/385.2 |
| 4,525,407 | 6/1985 | Ness | 428/138 |
| 4,573,991 | 3/1986 | Pieniak et al. | 604/385 A |
| 4,597,760 | 7/1986 | Buell | 604/397 |
| 4,597,761 | 7/1986 | Buell | 604/397 |
| 4,606,964 | 8/1986 | Wideman | 428/152 |
| 4,615,695 | 10/1986 | Cooper | 604/385 |
| 4,636,207 | 1/1987 | Buell | 604/370 |
| 4,642,110 | 2/1987 | Dudek | 604/385.1 |
| 4,643,730 | 2/1987 | Chen et al. | 604/390 |
| 4,657,539 | 4/1987 | Hasse | 604/385 A |
| 4,662,875 | 5/1987 | Hirotsu et al. | 604/370 |
| 4,662,877 | 5/1987 | Williams | 604/385 A |
| 4,685,916 | 8/1987 | Enloe | 604/385.2 |
| 4,699,620 | 10/1987 | Bernardin | 604/385.1 |
| 4,699,621 | 10/1987 | Stevens et al. | 604/367 |
| 4,701,170 | 10/1987 | Wilson et al. | 604/385.1 |
| 4,701,171 | 10/1987 | Boland et al. | 604/385.1 |
| 4,701,173 | 10/1987 | Zehner et al. | 604/367 |
| 4,701,174 | 10/1987 | Johnson | 604/387 |
| 4,701,175 | 10/1987 | Boland et al. | 604/385.1 |
| 4,704,114 | 11/1987 | Wilson et al. | 604/385.1 |
| 4,718,900 | 12/1988 | Boland et al. | 604/385.1 |
| 4,747,846 | 5/1988 | Boland et al. | 604/396 |
| 4,756,709 | 7/1988 | Stevens | 604/385.2 |
| 4,770,656 | 9/1988 | Proxmire et al. | 604/397 |

FOREIGN PATENT DOCUMENTS 0155515  10/1985  European Pat. Off. .

Primary Examiner—Randall L. Green
Assistant Examiner—K. M. Reichle
Attorney, Agent, or Firm—Douglas L. Miller

[57] ABSTRACT

A method is disclosed for making a fastener landing zone within a selected area on the front waist panel of a diaper. The front waist panel and a rear waist panel are stretchable in a cross-body direction, the rear panel having elongated ears bearing mechanical fasteners on inner, body-facing surfaces thereof which are releasably engageable with mechanical fasteners provided on the landing zones. The landing zones are shaped, sized and oriented on the front waist panel so as to impart a tensile force distribution pattern thereacross, directing tensile stresses away from the leg and waist openings while providing a band of abdominal support across the front waist panel between the landing zones.

9 Claims, 7 Drawing Sheets

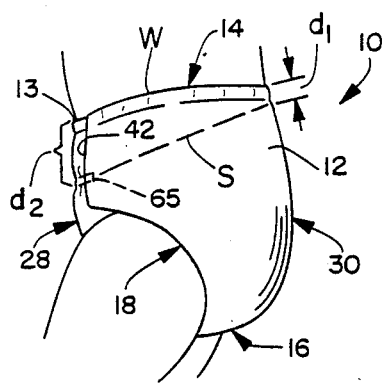
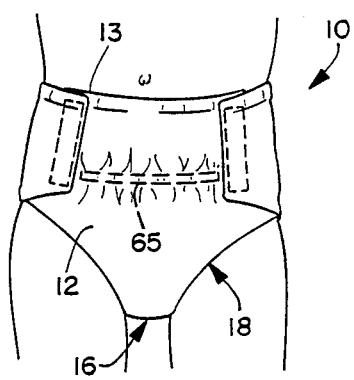
FIG. 4          FIG. 5
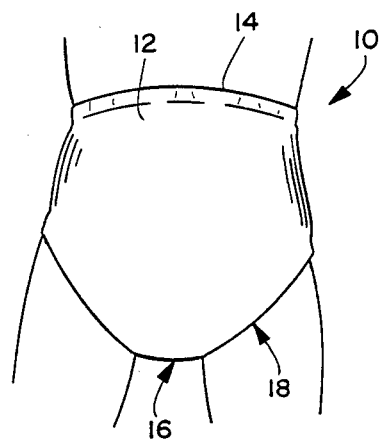
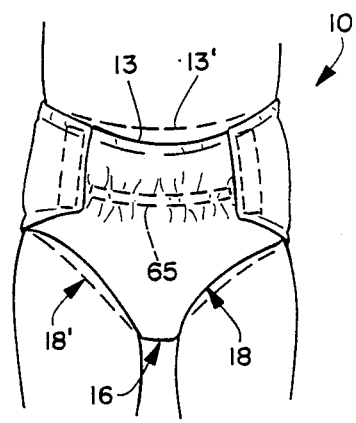
FIG. 6          FIG. 7

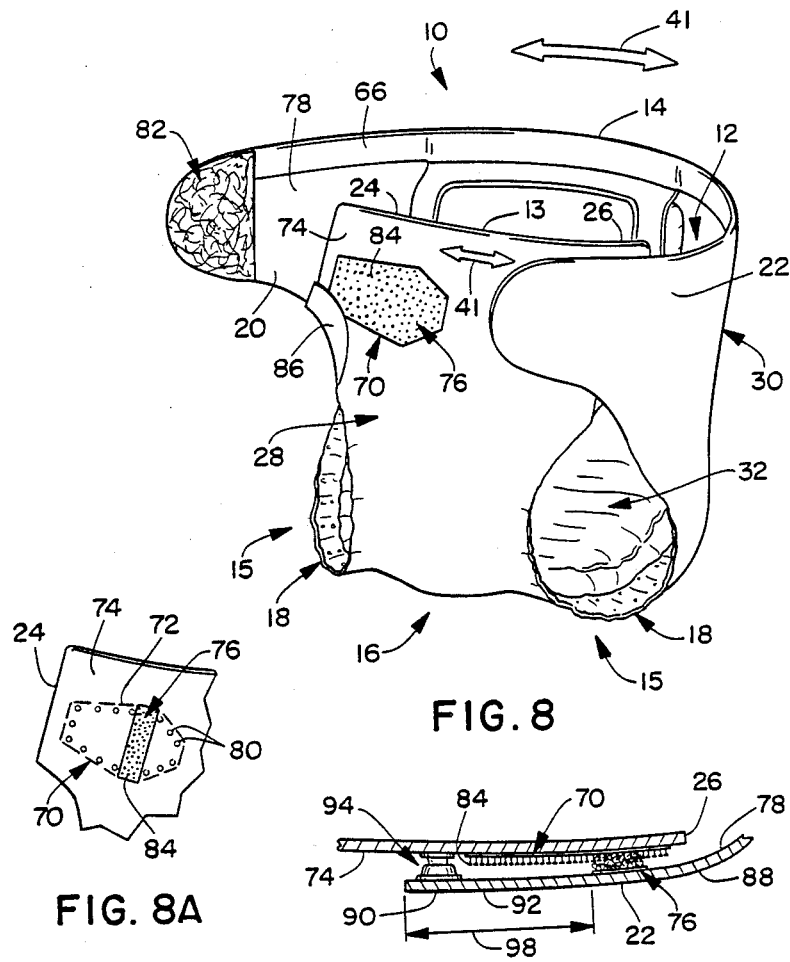
FIG. 8
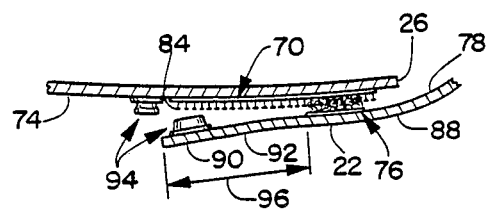
FIG. 8A
FIG. 9A
FIG. 9B

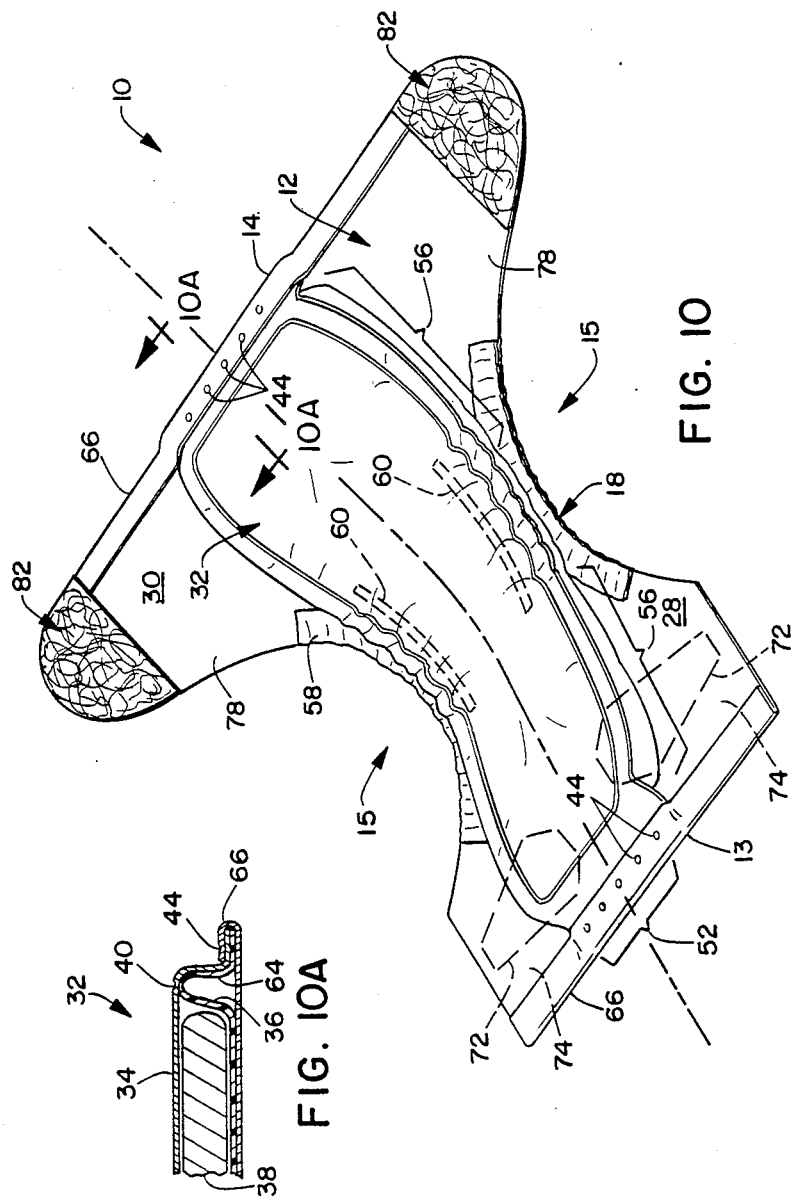

METHOD OF REDUCING FASTENER IRRITATION AND WAIST DROOP IN A DISPOSABLE DIAPER

TECHNICAL FIELD

The present invention relates, generally, to the field of disposable garments utilized for the absorption and containment of urine and other bodily exudates. More particularly, the present invention relates to disposable infant and adult diapers.

BACKGROUND OF THE INVENTION

This application is an improvement over U.S. Pat. No. 4,701,175, assigned to the assignee of the instant application. Disposable garments are generally well known in the art and have become an important and an essentially indispensable sanitary protection item, most particularly in the field of infant and child care where disposable diapers provide for the absorption and containment of urine and other bodily exudates. Present commercially available disposable diapers are generally unitary, preshaped and prefolded, and comprised of a porous facing layer and a fluid impervious backing sheet with an absorbent material disposed therebetween. These presently available disposable diapers have met a particular need and have become ever increasingly popular. However, even though the present available disposable diapers have achieved a certain degree of efficiency and effectiveness, several drawbacks remain that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes.

The typical disposable diaper has a three-layer composite structure comprising a liquid permeable bodyside inner liner, a liquid impermeable outer cover and an absorbent batt sandwiched between the liner and the cover. Materials now in general use for the three principal elements of a disposable diaper include various types of nonwoven fabrics for the bodyside liner, a thin thermoplastic film for the outer cover and cellulosic fluff for the absorbent batt. Examples of present disposable diapers are taught in U.S. Pat. No. 4,324,245 to Mesek, et al., U.S. Pat. No. 3,196,874 to Hrubecky, and U.S. Pat. No. 4,050,462 to Woon, et al.

Other prior art diaper constructions, disclosed in the references listed below, have sought to provide waste containment with a reusable diaper holder receiving an absorbent structure, to-wit:

1. U.S. Pat. No. 3,658,064 to Pociluyko and U.S. Pat. No. 3,370,590 to Hokanson, et al.;
2. U.S. Pat. No. 4,425,128 to Motomura;
3. U.S. Pat. No. 2,141,105 to Eller;
4. U.S. Pat. No. 4,397,646 to Daniels, et al.;
5. U.S. Pat. Nos. 4,597,761, 4,496,360 and 4,597,760.

U.S. Pat. No. 4,166,464 to Korpman, discloses an elastic fluid impermeable backing film laminated to an absorbent layer to ostensibly provide enhanced conformability to the body surface.

U.S. Pat. Nos. 4,355,425 to Jones, et al. and 3,644,157 to Draper disclose disposable stretchable nonwoven panties containing small crotch pads unsuitable for absorbing and containing body wastes.

Even where prior art designs have attempted to use impermeable elastic film barriers, there has been inadequate recognition of the functional problems associated with an elastic outer cover. Further, costly woven diaper holders or overpants, designed to be waterproof and reusable, do not offer disposability.

U.S. Pat. No. 4,586,199 to Birring discloses an elastic brief for use with a conventional disposable diaper. The brief is provided with front and rear crocheted elastic pieces which exert increased pressure along the sides of the underlying diaper to ostensibly hold it in place and seal the edges of the diaper against the body. The crocheting of the brief, to which the diaper is not physically attached, is looser in a central area in the front and back pieces to concentrate greater tension along the sides of the diaper at the legs and waist. This increased stress along the sides can lead to undesirable pinching by the garment at the legs and waist openings, leaving red marks and abrasions on the skin.

British patent application No. 2,185,383, published July 22, 1987, discloses an integral unitary disposable diaper having elasticized leg openings and fastening tapes with a tapered user's end, ostensibly for wearer comfort and easier handling during application thereof. The use of an elastomeric outer diaper cover is not disclosed in this document.

U.S. Pat. No. 4,701,175, assigned to the instant assignee, discloses a form-fitting, self-adjusting disposable garment comprising an elastomeric nonwoven outer cover having an absorbent insert structure attached and integrated thereinto.

Although the above-mentioned prior art garments are provided with elasticized leg and/or waist openings, there is still a tendency for the garment to blouse outwardly from the body at the hip and abdominal regions and to sag downwardly in the abdominal region. There is also a further tendency for tensile stresses to concentrate undesirably along the leg and waist openings of the garment. Thus, there remains a need for an anatomically form-fitting, generally self-adjusting disposable garment which provides additional support to keep the garment from sagging at the waist and drooping at the lower abdomen.

SUMMARY OF THE INVENTION AND ADVANTAGES

According to the invention, there is disclosed a method of making a fixed fastener landing zone on an appointed elastomeric surface of a waste-containment garment. The method comprises the steps of providing absorbent means adapted for absorbing and containing body wastes and providing an elastomeric nonwoven outer cover adapted for holding the absorbent means in a selected bodily registration when the garment is securely worn. The outer cover is provided with front and rear waist panels resiliently stretchable in a cross-body direction essentially transverse to a line centered on the longitudinal axis of said garment. An intermediate crotch panel separates the waist panels from one another and a pair of sides extend between and interconnect the waist panels, delimiting a pair of elastically contractible or expansible leg openings along the sides of the crotch panel and delimiting front and rear longitudinally opposed pairs of ears separated from one another by the crotch panel and comprising outermost lateral portions of the front and rear waist panels, respectively. Corresponding ones of the front and rear pairs of ears are engageable with one another to define an elastically contractible or expansible waist opening and the ears are provided with elongated shapes presenting inner, body-facing surfaces superposable on externally-facing surfaces of the front pair of ears. Fastening means are provided on the inner surfaces of the rear pair of ears and inelastic landing zones are appointed on given areas of the external surfaces, fastening means being provided on the landing zones to present cooperating fastening means releasably engageable with those provided on the rear ears. The landing zones are selectively shaped, sized and then oriented on the external surfaces, restricting the stretchability thereof within the given areas and thereby imparting a tensile force distribution pattern across the front waist panel which directs tensile stresses away from the leg and waist openings while providing a band of abdominal support across the front waist panel between the landing zones when the garment is securely worn.

In a preferred embodiment of the invention, the landing zones are truncated inwardly toward the centerline and have hook and loop mechanical fastening tapes provided thereon.

In a further preferred embodiment, the shape and orientation of the landing zones is selected to direct tensile stresses away from the leg and waist openings along the abdominal band of support.

BRIEF DESCRIPTION OF THE DRAWINGS

A preferred embodiment of the disclosed invention can be seen in the following drawings:

FIG. 4 is a side view of the disposable absorbent garment of the present invention shown secured around a baby;

FIG. 5 is a front view of the disposable absorbent garment of the present invention shown secured around a baby;

FIG. 6 is a back view of the disposable absorbent garment of the present invention shown secured around a baby;

FIG. 7 is a front view of the disposable absorbent garment of the present invention showing the disposition of the garment on the wearer after being worn for a period of time;

FIG. 8 is a perspective view of the garment of the present invention, showing fastener landing zones of the present invention;

FIG. 8A is a partial perspective view of a fastener landing zone constructed in accordance with the present invention;

FIG. 9A is a sequential view showing an alternative fastening system constructed in accordance with the present invention;

FIG. 9B is a sequential view of FIG. 9A;

FIG. 10 is an internal perspective view of the garment of the present invention;

FIG. 10A is a sectional view of cross—section 10A—10A of FIG. 10;

DETAILED DESCRIPTION OF THE PREFERRED EMBODIMENTS

Referring now to the figures, there are shown one or more preferred embodiments to the present invention as would be used in a disposable diaper. As used herein, the term disposable diaper refers to articles which absorb and contain liquid, and more specifically, refers to absorbent articles which are placed against or in proximity to the human body to absorb and contain the various solid or liquid wastes discharged therefrom, for example, urine and feces and, further, which articles are intended to be discarded after a single use (that is, they are not intended to be laundered or otherwise restored and reused). A "diaper" is a garment generally worn by infants or incontinent persons, which is drawn up between the legs and fastened about the waist of the user. It should be understood, however, that the present invention is also applicable for use in other disposable absorbent articles used as training pants and the like.

Figure 2:
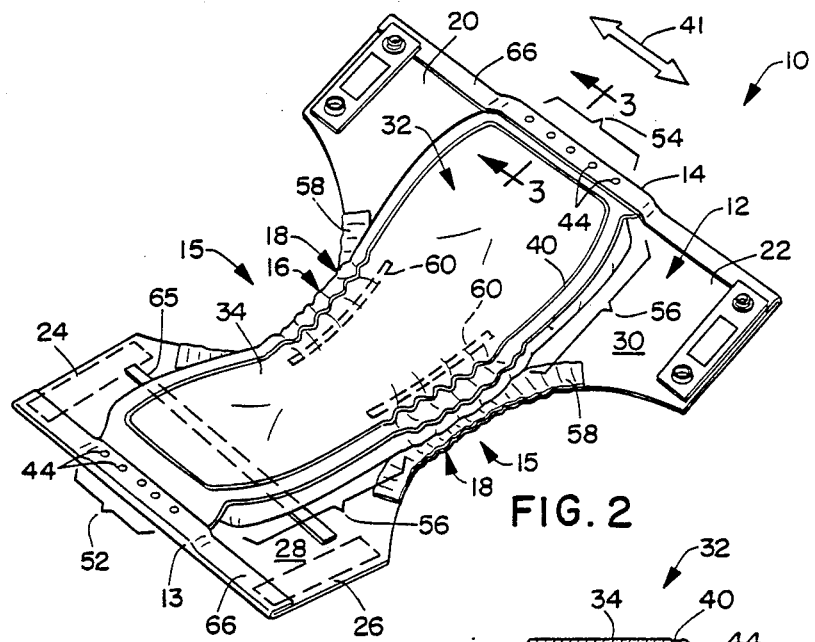
FIG. 2 is an internal perspective view of the invention shown prior to wear.

Referring to FIG. 2, according to the instant invention, there is provided an anatomically form-fitting, generally self-adjusting disposable absorbent garment, generally shown at 10, such as a disposable diaper, comprising an elastomeric outer cover, generally indicated at 12, including opposed front 13 and rear 14 waist sections together defining a waist opening and a pair of sides generally shown at 15 extending between and interconnecting the waist sections. A crotch section, generally indicated at 16, is situated between a pair of leg openings 18 delimited along said sides 15 at outermost portions of said crotch section 16. Ear portions 20, 22, 24, 26 are also delimited along the sides 15 generally between the opposed waist sections 13, 14 and each of the leg openings 18, respectively, with longitudinally opposed pairs 20, 24 and 22, 26 of said ears being engageable with one another about the body of a wearer. The outer cover 12 preferably has a generally hourglass or T-shaped configuration, with the leg openings 18 cut-out from the sides 15 thereof, defining a front waist panel 28 having a laterally opposed front pair of ear portions 24, 26 in conjunction therewith and a rear waist panel 30 having another laterally opposed rear pair of the ear portions 20, 22 in conjunction therewith.

The front 28 and rear 30 waist panels are separated from one another by the crotch section 16, which is narrowed due to the converging leg cut-out openings 18 and extend between the laterally opposed front and rear pairs of ears, respectively, between the corresponding waist sections and the leg openings as shown in the figures.

Figure 3:
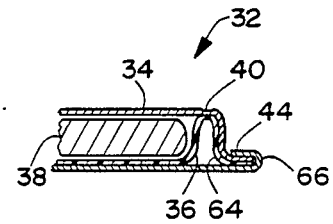
FIG. 3 is a sectional view of cross-section 3—3 of Figure 2.
Figure 11:
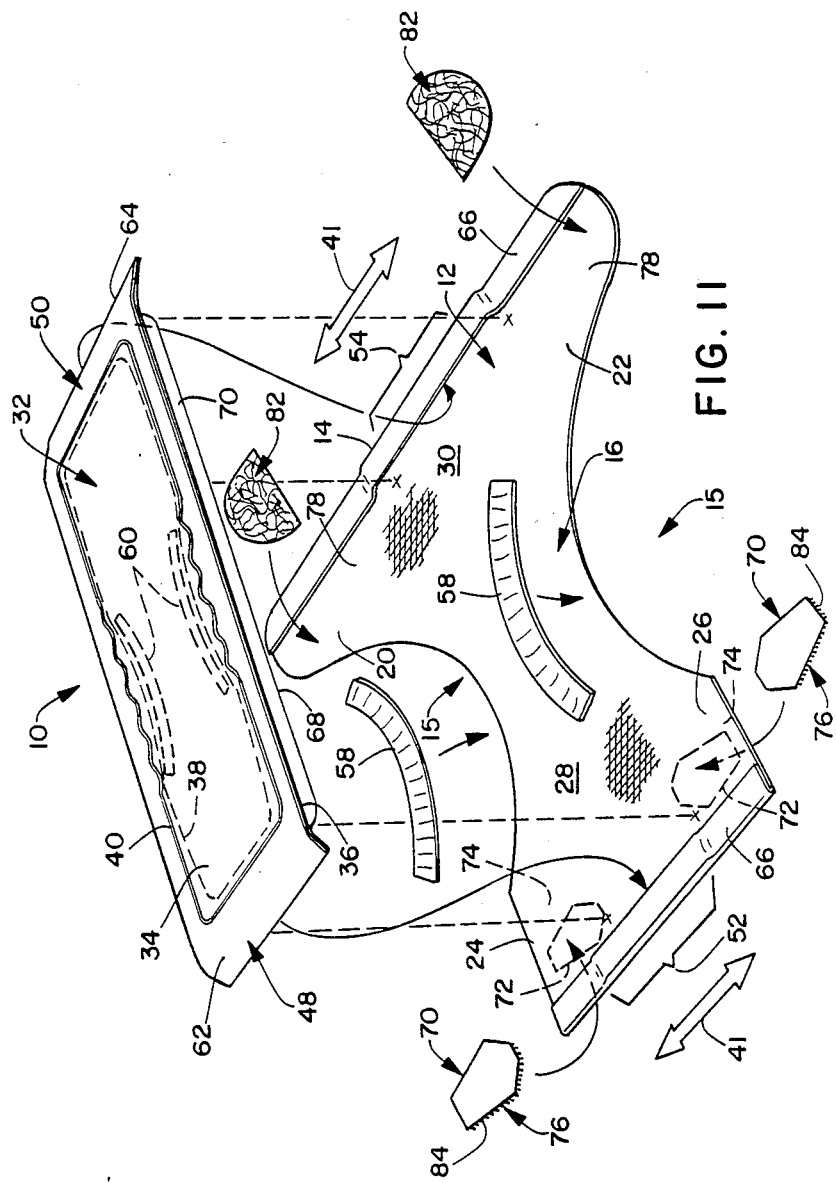
FIG. 11 is an exploded perspective view of the garment of the present invention.

With continuing reference to FIG. 2, and also to FIG. 3, there is depicted an absorbent insert structure, generally indicated at 32, substantially superposable on the front 28 and rear 30 panels and the crotch section 16 of the outer cover 12 for absorbing and containing bodily exudates, particularly urine and feces. The absorbent structure 32 includes: a liquid permeable bodyside liner 34, for example, a commercially available pattern-bonded, spunbonded polypropylene web that may have a basis weight of from about 0.2 to 0.8 oz./yd$^2$.; a liquid impermeable barrier 36, for example, a commercially available plastic film of polypropylene or the like; and an absorbent core 38 disposed therebetween. As shown in FIG. 11, the absorbent structure 32 is in the form of a separate insert, typically of materials which are substantially nonstretchable, attached and integrated into the resiliently stretchable outer cover 12, preferably using autogenous bonds of the type generated thermally or ultrasonically, while allowing substantially unrestricted functional stretchability of the outer cover in a manner hereinafter described. A preferably continuous ultrasonic or thermal perimeter bond 40 sealingly secures the absorbent structure 32 together to prevent leakage therefrom by bonding the liner 34 and barrier 36 peripherally to one another, making the liner and barrier coterminous with one another, about the absorbent core 38 disposed therebetween. It is important that the materials of the barrier 36 and liner 34 be compatible with one another and with the material of the outer cover 12 for autogenous bonding. Accordingly, polypropylene and other polyolefins or polyolefin blends have been found to be suitable and economical polymeric materials for use in the liner, barrier and outer cover of the instant garment 10.

The outer cover 12 generally comprises an air-permeable, i.e., "breathable", elastomeric nonwoven material, particularly a stretch-bonded laminar fabric wherein an elastic nonwoven web is joined to one or more gatherable nonwoven webs of the type described in greater detail herein. Preferably, the nonwoven laminate is resiliently stretchable from about 20 to about 200 percent in an essentially cross-body direction 41 which is transverse to a longitudinal axis of the garment.

The longitudinally opposed ears 20, 24, 22, 26, which are engageable about a wearer, are releasably fastenable with one another, forming full-length closures extending substantially from the waist to the leg openings of the outer cover. The full-length closures further provide dimensional integrity to the resiliently stretchable garment during various and even extreme bodily movements and positions of the wearer. Since the garment is form-fitting and self-adjusting, it does not gap or collapse at the hip and waist regions. The various fastening systems used in the invention are also detailed herein.

Preferably, the waist sections 13, 14 of the outer cover 12 have the insert 32 attached and integrated thereinto by attachment means according to the present invention as will be set forth more fully below.

With respect to the attachment means of the present invention as shown in FIGS. 2 and 3, it is important to minimize the number of bonds and total bond area used in integrating the relatively unstretchable absorbent insert to the stretchable outer cover or, where forming hems, the number of bonds used to bond the outer cover to itself. The Applicants have discovered that the number of bonds correspondingly affects the stretch elongation in the elastomeric component that is bonded. Not only does a lesser number of bonds result in less stretch loss, but the greater the spacing apart of bond points, the less stretch elongation is affected. Accordingly, bonding patterns should be selected that significantly reduce the amount of stretch lost by means of the density and spacing of the bond points. Specifically, the lower the number and density of the bonds 44 for attaching and integrating the insert 32 along the waist sections 13, 14, the less stretch is inhibited in said waist sections. For example, if the waist section is stretchable in a cross-body direction and the insert is attached thereto at two points lying on a line extending also in said cross-body direction, then the stretchability of the outer cover waist section along that line is restricted between those two points of attachment by the least stretchable element present between those points, such as the liner and barrier of the insert or, further, the absorbent core which may be glued to the barrier with, e.g., hot melt construction adhesive. Similarly, the insert may also be attached and integrated at the crotch section.

Therefore, the garment of the present invention includes attachment means for attaching and integrating the absorbent insert structure 32, which is generally inelastic, into the relatively resiliently stretchable elastomeric outer cover which is used for positioning the insert in a selected bodily registration, while allowing substantially unrestricted functional stretchability thereof. Thus, the total garment is maintained anatomically form-fitting and generally self-adjusting.

These and other objectives have heretofore been addressed by Applicant's prior copending application Ser. No. 947,947, filed Dec. 31, 1986, now U.S. Pat. No. 4,770,656, the entire disclosure of which is expressely incorporated by reference herein and relied upon. Referring to FIGS. 2 and 4–7, full-length closures of the type disclosed in this referenced application may have cooperating primary closures, e.g., snaps, adjacent the waist and leg openings of each full-length closure, and cooperating secondary closures, e.g., hook and loop tapes, extending between each of the cooperating pairs of primary closures.

The instant garment 10 is generally constructed and assembled as shown in FIG. 2 and, with respect to other alternative embodiments, in FIGS. 10 and 11. The bonds 44 attach and integrate the opposed longitudinal ends 48, 50 of the absorbent insert 32 to said outer cover 12 at selected front 52 and rear 54 waist attachment zones along said front 13 and rear 14 waist sections, respectively, defining one or more free-span zones 56 underlying said insert 32 wherein the functional stretchability of said outer cover in said free-span zone 56 is substantially unrestricted. It will be understood that where the insert 32 is integrated only at the waist attachment zones 52, 54, i.e., not at the crotch section 16, the free-span zone wherein the outer cover stretchability is substantially unrestricted underlies the entire longitudinal span of the absorbent insert 32. Significantly, the free-span zone 56 also includes those portions of the waist sections 13, 14 not included in the waist attachment zones 52, 54. It will also be understood that the insert 32 may be adequately held by the outer cover 12 in registration with the body of the wearer without significant sideways shifting. Additional bonding of the insert in the free-span zone 56 to the front 28 or rear 30 panels or the crotch section 16 is not required.

Although the free-span zones 56 can be provided in either of the front 28 and rear 30 panels, it is important that the rear panel 30 have substantially unrestricted stretch properties from waist to leg across the lateral span of the rear panel 30 from one of the rear pair of ears 24 to the other ear 26. Cross-body direction stretch of the crotch section 16 of the outer cover 12 during use is minimally required so that bonding of the insert 32 at or near the leg openings 18 of the crotch section 16 does not significantly affect the overall cross-body stretch properties of the outer cover, that is, the ability to be resiliently stretchable across the area defined by the front 28 or rear 30 waist panels.

The breathable outer cover 12 which, among other functions, holds the insert 32 in proper bodily registration, is not itself required to provide a liquid waste-containment barrier, unlike the prior art. In fact, application Ser. No. 947,942 also teaches a garment having a disposable insert which may be removed and replaced using snaps or the like, so that the outer cover becomes reusable, in this regard, the garment of the instant invention could also have a reusable outer cover and disposable insert system.

Referring again to FIG. 11, the absorbent insert 32 may further comprise at least one but preferably a pair of front 62 and rear 64 waist attachment flaps respectively situated at the opposed longitudinal ends 48, 50 of the insert 32. The flaps 62, 64 extend longitudinally from and contiguous with the liner 34 beyond the terminal ends of the absorbent composite 38, the flaps being bonded or otherwise attached to said front 13 and rear 14 waist sections, respectively, in said waist attachment zones 52, 54. The front 13 and rear 14 waist sections preferably have finished waist hems 66 along the waist opening wherein the waist attachment flaps 62, 64 are entrapped and bonded. The waist hems 66 comprise inwardly folded-over edges of said waist sections 13, 14. The waist attachment flaps 62, 64 (FIG. 11) may comprise coextensions of the barrier 36 and liner 34 or may comprise extensions of either the barrier 36 or liner 34 alone. Although the flaps 62, 64 typically comprise a nonwoven liner and plastic film materials that are not inherently stretchable relative to the outer cover 12, the flaps 62, 64 themselves need not be contiguous with the liner or barrier material.

Referring to FIGS. 2, 4, 5 and 7, according to the instant invention, there is provided an abdominal support band 65 attached to the front waist panel 28 and extending in the essentially cross-body direction indicated by arrow 41 across at least the central portion of the front waist panel 28. The abdominal support band 65 has a modulus of elasticity which is selected to either be greater or less than the modulus of elasticity of the front waist panel 28 in the essentially cross-body direction 41, depending on the desired fit characteristics of the garment 10. Where contractability of the garment 10 is employed in order to achieve the desired fit for a range of body sizes, the outer cover 12 will be sized to fit larger body sizes within the given range and then supplemental elasticization in the waist and legs is provided to shorten the garment openings to fit the torso and thighs of a particular wearer. In this case, the supplemental elastics, such as the leg elastics 58 and the abdominal support band 65, must have a modulus of elasticity selected to provide a greater tension than the remaining portions of the outer cover to which the elastics 58, 65 are not attached. Conversely, where expansibility of the garment is employed to achieve the desired fit characteristics of the outer cover, the outer cover 12 is sized to fit smaller sized individuals within the given range of sizes, utilizing the inherent stretchability of the outer cover material to expand and accommodate the dimensions of the torso and legs of a particular wearer. The abdominal support band 65 may be an extruded elastomeric film or nonwoven material which, in the case where the band 65 has a greater tension than the remainder of the front panel, be attached to the front panel in a stretched condition with, for example, adhesive, or, in the case where the support band 65 has a lower modulus of elasticity than the remainder of the front panel 28, the support band may comprise a band of the outer cover which has been bonded, either autogenously by thermal or ultrasonic means, or adhesively by attaching an adhesive piece to the front waist panel 28, thereby negating the stretch properties of the band which is thus bonded.

Figure 1:
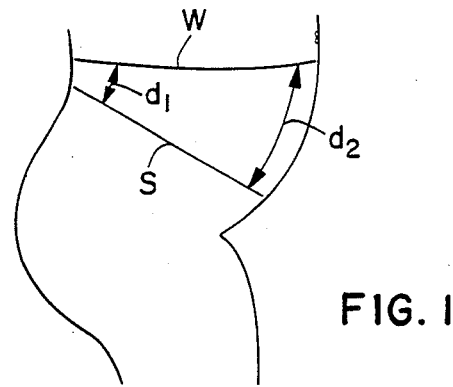
FIG. 1 is a schematic view indicating the lines of support of the present invention relative to the body.

Referring to FIG. 1, the waist opening W defined by the front 13 and back 14 waist sections of the diaper is the desired positioning for proper fit of the garment of the present invention. The natural support line for the diaper, designated by the letter S, runs from the small of the back, over the hip and on the lower side of the protruding stomach. The distance from the small of the back up to the waist is represented by the designation $d_1$ and $d_2$ represents the distance from the support line S to the waist opening W. The distance $d_2$ is longer than the distance $d_1$ by about 1 to 3 inches. By providing disposable diapers with a support band located about 1 to 3 inches below the waistband, the diaper will be held in position better with less front panel drop than is seen in currently available commercial diapers. The panels 28, 30 will be held up from below the support band. The support band can take a number of forms. First, in a conventional unitary disposable diaper, the band could be an elastomeric material stretched then attached to the outer cover so as to contract the plastic film outer cover and provide a contractible force along the support lines (not shown).

The band 65 can be located in the front waist panel only, the rear panel 30 as well or a portion only of the front and back. Elastic waistbands currently provided in disposable diapers do not serve the function of the instant support band 65 since they provide mainly an aesthetic nonsupporting waist line appearance, e.g., along the line W.

Referring again to FIG. 2, additional elastication or bonding between other areas of the outer cover 12 and absorbent insert 32 may be provided. Specifically, supplemental leg elastics 58 may be applied to outermost portions of the crotch section 16 around the inner curvature of the leg openings 18 to gather the garment 10 about the thighs of the wearer. Crotch elastics 60 may be applied to the liner 34 to cause the insert to more closely conform to the contours of the wearer's perineal region.

The leg elastics 58 preferably comprise a breathable elastomeric nonwoven laminate of the type described in said prior copending U.S. Pat. application Ser. No. 947,947 of applicant. The leg elastic members 58 function cooperably with the stretchable outer cover for gathering the leg openings 18 about the wearer and can be applied in varying tensions relative thereto by adhesive, autogenous or pressure bonding. Leg hems (not shown) may alternatively be formed at the curved leg openings 18 in addition to the waist sections 13, 14, resulting in increased tension due to the increased thickness of the elastomeric material of the outer cover at the folded over hem. For this purpose, additional elasticized gathers (not shown) of, e.g., FULLASTIC®, a trademarked extruded elastomeric film material sold by H. B. Fuller Company of Minneapolis, Minn., can be entrapped within the waist hems 66 and any leg hems (not shown) to provide such additional elastic gathering. Although the waist opening has heretofore been discussed in conjunction with waist hems 66 and optional waist elastics entrapped therein, a nonwoven elastomeric laminar material of the type described for the leg elastics 58 could be applied as a border strip (not shown) along the waist sections 13, 14 defining the waist opening.

As can be seen in FIG. 11, the barrier 36 closely surrounds the bottom 68, and sides 70 of the absorbent core 38 (shown in phantom) with the liner 34 extending across and contacting the top surface of the absorbent core 38, imparting a generally rectangular boat-shaped configuration to the insert 32. The bottom 68 of the barrier 36 may include one or more relaxed localized areas adjacent the bottom 68 of the absorbent core 38 to accommodate swelling of the core occurring during use with, for example, a hydrogel material. The perimeter bond 40 making the liner 34 and barrier 36 coterminous substantially around the absorbent core 38 may comprise either intermittent bonds or, preferably, a continuous autogenous, i.e., ultrasonic or thermal, bond. The perimeter bond 40 is preferably undulatory along the intermediate portion of the core 38, imparting a scalloped edge for greater flexibility therein.

Significantly, the absorbent structure 32 may be integrated into the outer cover 12 in the waist attachment zones 52, 54 while the outer cover is at least partially stretched in the cross-body direction 41. Preferably, the longitudinal length of the free-span zone 56 in the front 28 and rear 30 panels is at least about 2.5 inches or the longitudinal length between the waist and leg openings.

A preferred method of integrating the absorbent insert structure 32 into the resiliently stretchable breathable outer cover 12 and assembling the instant disposable absorbent garment 10 comprises the steps of providing the outer cover 12 with opposed front 13 and rear 14 waist sections, a central crotch section 16, front 28 and rear 30 waist panels extending between the crotch and the waist sections, prestretching the outer cover more than about 20%, preferably from about 20% to about 200%, in the cross-body direction 41 while superposing the insert 32 upon the outer cover, then bonding the longitudinally opposed ends 62, 64 of the insert to the waist sections 13, 14 in the selected waist attachment zones 52, 54, defining one or more free-span zones 56 allowing substantially unrestricted functional stretchability of the outer cover 12 underlying the free-span zones 56 (FIG. 10). One aspect of the present integration method comprises the step of inwardly folding over the outermost edges of the waist sections 13, 14 forming waist hems 66 entrapping the longitudinally opposed ends 62, 64 of the absorbent insert therein and bonding the opposed ends 62, 64 of the insert within the waist hems 66 at the waist attachment zones 52, 54 (FIGS. 10 and 11). As disclosed above, however, the waist opening may be elasticized by a breathable elastomeric nonwoven laminar border strip rather than elastomeric waist hems.

With respect to the physical properties required of the fastening system shown in FIG. 2, it has been found that the primary closures adjacent the leg and waist openings should have a peel strength from about 600 grams to about 2,500 grams, depending upon the outer cover material and the ability or strength of the parent or other user to open the closures. The secondary closures should have a shear strength greater than about 3,750 grams per square inch. The full-length closures maintain the dimensional integrity of the garments with minimal sagging of the waist or gapping and blousing at the hips during wear. The combination of desired peel and shear strength ranges for the fastening system shown in FIG. 2 is also applicable to the alternative fastening system shown by FIGS. 8-16, that is, the fastening system should have a combined peel strength in the 600 gram to 2,500 gram range and shear strength greater than about 3,750 grams per square inch, as determined by the measurement methods set forth in said application Ser. No. 947,947.

FIGS. 4-7 show a disposable diaper 10 of the instant invention as it would be worn by a baby wherein the disposable diaper has a neat, trim, anatomically form-fitting appearance when viewed from different perspectives. Particularly, there is shown in FIGS. 4, 5 and 7 the proper positioning of the diaper 10 on a wearer during use, as aided by the abdominal support band 65.

Referring to FIG. 4, the elasticized waist sections 13, 14 define a waist opening providing, at least in part a fit line W which corresponds to the lower umbilical region of a wearer, for optimal anatomical conformity and aesthetic appearance of the garment 10 when securely worn. Spaced from the waist sections 13, 14, the abdominal support band 65 extends angularly downwardly relative to said front waist section 13 defining, at least in part, a natural abdominal support line corresponding generally to a line extending anteriorly about the body from the dorsal side of the transtubercular plane over the iliac crests and across the abdominal hypogastric region of a wearer.

FIG. 7 illustrates the self-adjusting functionality of the diaper aided by the abdominal support band 65, as shown by the minimal extent the diaper moves or sags from an initial position as indicated by the dashed lines 18'and 13'after being worn by an infant for a period of time.

Although the abdominal support band 65 discussed above in conjunction with Figures 1, 2 and 4-7 does provide a natural support line corresponding to the lower abdominal region of the wearer, the support band 65 provides only a limited degree of distribution of the tensile stresses across the front waist panel when the diaper is worn. During wear, it is desirable to direct tensile stresses away from those portions of the leg and waist openings that typically experience red marking. The placement and positioning of a fastening system which is nonstretchable can reduce forces near the leg opening and direct forces across the outer cover to support the absorbent, especially when wet, resulting in reduced diaper sag and droop, as will be shown herein in conjunction with FIGS. 8-16.

Referring to FIG. 8, there is depicted a disposable diaper 10 having the absorbent structure 32 attached and integrated within the elastomeric nonwoven outer cover 12. The front 28 and rear 30 waist panels are resiliently stretchable in the cross-body direction 41 and are engageable with one another to define a waist opening along the uppermost edges of the waist sections 13, 14. The sides 15 extend between and interconnect the waist sections, delimiting the pair of leg openings 18. The leg openings 18 may be either elastically contractible to gather the garment about the legs of a wearer or may be expansible, depending upon the particular fit parameters desired. The rear pair of ears 20, 22 define elongated shapes presenting inner, body-facing surfaces superposable on externally-facing surfaces 74 of the front pair of ears 24, 26, as shown in FIG. 8. A pair of inelastic landing zones, generally indicated at 70, are appointed within given areas (shown by the phantom lines 72 in FIG. 8A, 10 and 11) of the external surfaces 74 of the front pair of ears. The landing zones 70 have fastening means, generally indicated at 76, provided thereon which are releasably engageable with fastening means, also indicated at 76, provided on the inner surfaces 78 of the rear pair of ears, as shown in FIG. 11. The landing zones 70 are selectively shaped, sized and oriented on the external surfaces 74 of the front ears so as to impart a tensile force distribution pattern directing stresses away from the leg 18 and waist openings defined by the waist sections 13, 14, while providing a band of abdominal support across the front waist panel 28 when the garment is securely fastened about a wearer, as will be appreciated with reference to the discussion herein.

Figure 12A:
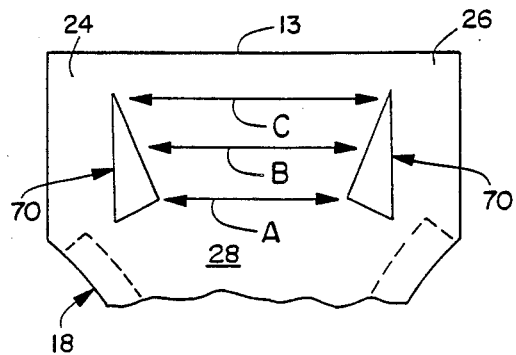
FIG. 12A is a schematic view of the front waist panel of the present invention.
Figure 12B:
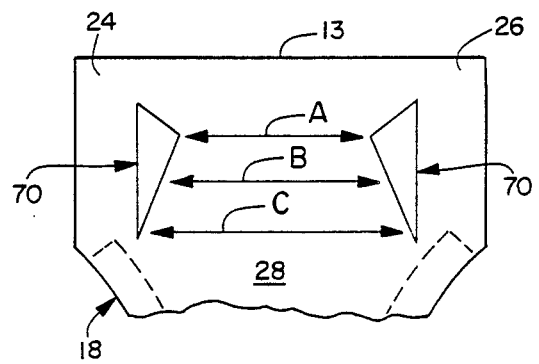
FIG. 12B is a schematic view of the front waist panel of the present invention.

Referring again to FIG. 8, the landing zones 70 may be shaped in a generally rounded or angular polygonal area. The width of the polygon (FIGS. 8 and 8A) narrows preferably, tapering in order to gradually concentrate forces away from the waist opening and the leg openings. The placement and positioning of the fastener landing zones 70, which are nonstretchable, define areas in a stretchable diaper, such as the front waist panel 28, which define regions of higher tensile forces therebetween, depending on the distances between points on the landing zones 70 and the stress/strain properties of the materials used for the outer cover 12. In this manner, tensile forces in the diaper can be directed to desired regions. Fastener position can, therefore, reduce forces near the leg openings and/or direct forces in the outer cover across an absorbent pad held therein to reduce diaper sag and droop. This is because a nonstretchable component bonded to a stretchable material eliminates stretch in the bonded region. When a fastener is bonded to a stretchable outer cover such as in the instant invention, the fastener shape generates zones where the outer cover must stretch to a greater extent and thus is at higher tension as defined by its stress/strain curve. Referring to FIG. 12A, triangularly shaped landing zones 70 direct forces across the front panel 28 to increase tension at the hips generally along the line A. The tension generated between the landing zones is proportional to the distance between fixed points on the landing zones, for example, the tension generated between end points of the segment A is greater than that generated along the line B, which is, in turn, greater than that generated along the line C. Such a landing zone placement operates to increase tension in the hip regions of the front panel 28. In similar fashion, the landing zone placement may be selected to increase tension at the waist opening, as shown in FIG. 12B wherein tension is greatest generally along the line A, with lines B and C representing lessening tensions approaching the leg openings 18. To increase tension in a localized region, it is necessary, as discussed above, to define a given area which represents a nonstretchable zone. This may be accomplished with either a bonded piece of material, or simply a bond pattern, as shown in FIG. 8A, wherein the given area 72 is surrounded by a series of autogenous, for example, ultrasonic bonds 80 conforming to the shape of the given area 72 and thereby defining the landing zones 70. The fastener landing zones 70 shown in FIGS. 8, 8A and 12C direct tensile forces away from both the leg and waist openings by providing the landing zones 70 with generally triangular shapes which direct forces along a central line A bisecting the landing zones, wherein the tensile forces generated along the line A are greater than those generated between the landing zones along the lines B (FIG. 12C).

Where the landing zone is delimited by a closed pattern of ultrasonic bonds 80, as shown in FIG. 8A, the hook component 82 of the fastening means 76 may be attached in a strip as shown and need not cover the entire landing zone 70, allowing smaller amounts of costly fastener material to be used; however, as shown in FIGS. 8 and 11, the landing zones 70 could comprise entire pieces of fastener material. The fastening means provided on the landing zones 70 and on the inner surfaces 78 of the rear pair of ears 20, 22, preferably comprises hook and loop fastening tapes of the type which are well known in the art and available from companies such as, for example, Velcro, U.S.A., Inc. Nevertheless, it will be appreciated by those skilled in the art that other forms of mechanical or even adhesive fastening means could be used in the diaper of the present invention. Preferably, where hook and loop fasteners are used, the loop portion 82 should be located on the inner, body-facing surfaces 78 of the rear pair of ears 20, 22 and the harsher hook portions 84 should be located on the landing zones 70, as shown in FIG. 11 to minimize potential skin contact therewith. It is preferable to further isolate the harsh hook portions 84 from possible contact with the skin of a wearer's leg by forming flaps 86 which cover a lower marginal portion of the hook material. The flaps 86 may be formed by outwardly folding over marginal edges of the leg openings 18 adjacent the front waist panel 28, as shown in FIG. 8.

Alternatively, the front ears may be further elongated in a cross-body direction and the landing zones tapered and elongated so that their width narrows distally in a direction away from the centerline, thereby enabling the fastening means to be secured together along substantially the full tapered length of the landing zones to provide a longer closure along the sides of the garment, where desired, between the front and rear waist panels from the leg openings to the waist openings, while avoiding fastener-skin contact (not shown).

Figure 12C:
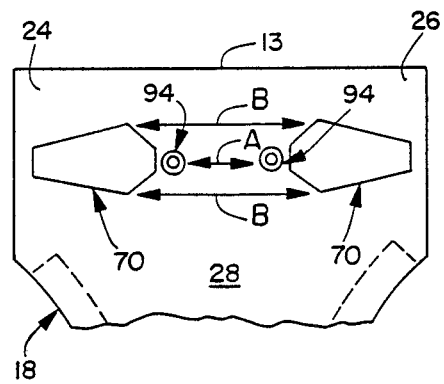
FIG. 12C is a schematic view of the front waist panel of the present invention.

Referring to FIGS. 9A, 9B and 12C, there is shown an alternative to the fastening system constructed in accordance with the present invention. Not only is it possible to minimize the amount of material used for the hook component 84 used as a mechanical fastening element on the landing zone 70 (FIG. 8A), but it is also possible to minimize the amount of loop material 82 utilized on the body-facing surfaces 78 of the rear pair of ears, of which a representative ear 22 is illustratively shown. With further reference to FIGS. 9A and 9B, there is shown an adjustable combination fastening system wherein the rear pair of elongated ears 22 comprise proximal portions 88 equidistantly spaced from the centerline, user end portions 90 spaced distally from the proximal portions 88 and elastomeric medial portions 92 adjustably spacing the user portions 90 from the proximal portions 88. The hook component 84 of the mechanical fastening means 76 is provided on the landing zones 70 appointed on the externally-facing surfaces 78 of the front ears 24, 26, of which a single front ear 26 is illustratively shown in FIGS. 9A and 9B. Fixed-position mechanical fastening means, such as the snaps generally indicated at 94, are provided on the external surface 74 of the front ear 26 and the bodyside surface 78 of the rear ear 22. The hook 84 and loop 82 components on the landing zones 70 and the proximal portion 88 of the rear ear 22, respectively, comprise variable-position mechanical fastening means which are initially engaged when fastening the diaper garment 10, as shown in FIG. 9B. Once the strip of loop component 82 is engaged at a desired location with the hook component 84 on the landing zones 70, the user end 90 bearing the snap element 94 may be stretched to cover the remainder of the hook component 84, as shown by the sequential arrows 96 (FIG. 9B) and 98 (FIG. 9A) sufficiently to allow the mating snap elements 94 to be engaged with one another. In this manner, the medial portion 92 of the rear ear imparts a certain degree of adjustability to the mechanical fastening means, while providing a secure fixed snap engagement which is more resistant to tampering by a child. FIG. 12C illustrates the placement of the fixed-position fastening means 94 with respect to the landing zones 70. In this arrangement, the fixed-point fastening means 94 are functionally a part of the landing zones 70 and define a shortest distance A therebetween wherein the tensile forces in the front waist panel 28 concentrate and are of the greatest magnitude relative to the tensile forces elsewhere between the landing zones, as represented by the distances B in FIG. 12C.

FIGS. 10 and 10A show an internal perspective view of the assembled garment having the preferred fastening arrangement of the present invention. Other nonfastening structures are indicated which are similar to those discussed in conjunction with FIG. 2.

A preferred method for making the landing zones of the present invention is further illustrated by reference to the exploded perspective view of the garment shown in FIG. 11. The method comprises the steps of providing an absorbent structure 32 adapted for absorbing and containing body wastes and providing an elastomeric nonwoven outer cover 12 adapted for holding the absorbent structure 32 in a selected bodily registration when the garment 10 is securely worn. The outer cover 12 is provided with front 28 and rear 30 waist panels resiliently stretchable in a cross-body direction 41 and an intermediate crotch panel 16 separates the waist panels 28, 30 from one another, with a pair of sides 15 extending between and interconnecting the waist panels. Delimited along the sides 15 are a pair of leg openings 16 which may be elastically contractible by means of the supplemental gathers 58 or may be sized so that elastic expansibility is relied upon for appropriate leg fit. Fastening means, specifically the soft loop component 82, are provided on the internally-facing surfaces 78 of the rear pair of ears 20, 22. Inelastic landing zones 70 are appointed on given areas 72 of external surfaces 74 of the front pair of ears 24, 26, with hook components 84 of the fastening means provided on the landing zones 70, which are formed with a selected shape and size. The landing zones 70 are then oriented and bonded, such as with the autogenous bonds 80 shown in FIG. 8A, onto the given areas 72 of the external surfaces 74.

Figure 13:
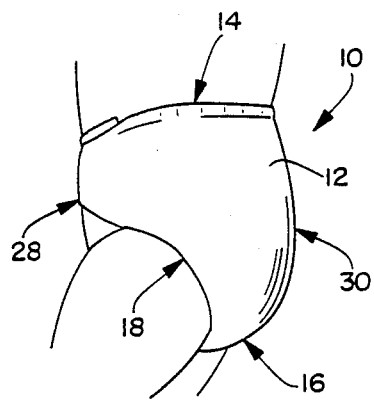
FIG. 13 is a side view of a disposable absorbent garment shown secured about a wearer by the fastening system of the present invention.
Figure 14:
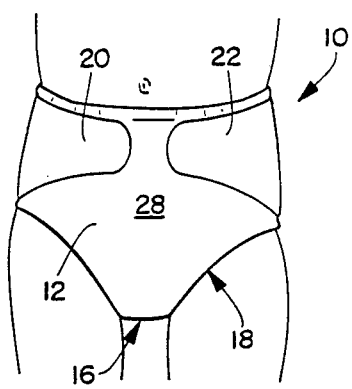
FIG. 14 is a front view of a disposable absorbent garment shown secured about a wearer by the fastening system of the present invention.
Figure 15:
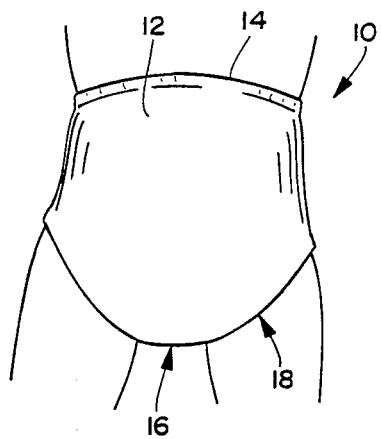
FIG. 15 is a back view of a disposable absorbent garment shown secured about a wearer by the fastening system of the present invention.
Figure 16:
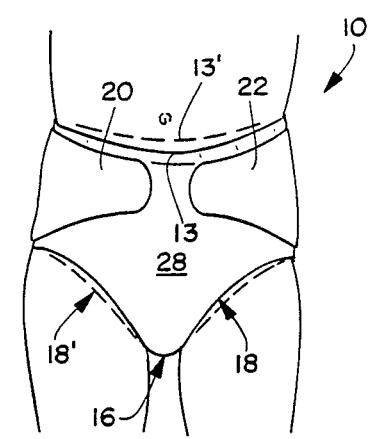
FIG. 16 is a front view of a disposable absorbent garment secured about a wearer by the fastening system of the present invention, showing the disposition of the garment on a wearer after being worn for a period of time.

Also with reference to FIGS. 13-16, the subject fastening system is integrated into the diaper design to function cooperatively with the other components of the diaper 10 and requires similar familiar hand motions as conventional tape systems, taking the same time to fasten. It also utilizes materials with which users are comfortable and familiar, that is, snaps and hook and loop fasteners. The subject diaper fastening system stays fastened, is refastenable, is contamination-free, contributes to the fit characteristics of the diaper and does not leave tell-tale red marks on the skin of a wearer. Moreover, the subject fasteners rely more on the inherent stretch characteristics of the outer cover by increasing the outer cover tension across the front waist panel 28. They also more conveniently place the fastener target on the front panel 28 of the diaper 10 and offer an easy one-step closure. The elongated ears 20, 22 are easily handled and apparent tightness of the garment is reduced while offering a gentler waist and leg fit. The instant invention reduces droop and holds the absorbent structure in a desirable position against the wearer as seen in FIGS. 13, 14, 15 and, particularly in FIG. 16.

Turning now to the outer cover 12 of the present invention, which is preferably made from a resiliently stretchable elastomeric nonwoven laminar material having a stretchability of from about 20 percent to about 200 percent. The term stretchability as used herein is defined by the following relationship:

$$\text{stretchability} = ((\text{final dimension} - \text{initial dimension})/\text{initial dimension}) \times 100\%$$

Since the outer cover 20 is also resilient, the outer cover returns essentially to its initial dimension when the stretching force is removed.

One such resiliently stretchable material is disclosed in U.S. Pat. No. 4,663,220 to Tony J. Wisneski and Michael T. Morman, assigned to the assignee of the present application, entitled "Polyolefin-containing Extrudable Compositions and Methods for their Formation Into Elastomeric Products", the entire disclosure of which is incorporated herein by reference and relied upon. That patent provides extrudable elastomeric compositions which, after extrusion, solidify to form elastomeric products such as, for example, fibrous nonwoven elastomeric webs. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A"and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.7 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. Pat. application, Ser. No. 760,437 in the name of Jack D. Taylor and Michael J. Vander Wielen and assigned to the assignee of the present application, entitled "Composite Elastomeric Material and Process for Making the Same", the entire disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. Pat. No. 4,657,802 to Michael J. Morman, assigned to the assignee of the present invention and entitled "Composite Nonwoven Elastic Web", the entire disclosure of which is incorporated herein by reference and relied upon. That patent is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The patent also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. Pat. No. 4,657,802 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spunbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. Pat. No. 4,657,802 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, non-stretched state, is composed of a nonwoven elastic web that is joined to a fibrous nonwoven gathered web which has been gathered as a result of the nonwoven elastic web having been relaxed from an elongated stretched, biased length to a relaxed, unbiased non-stretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A"may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

U.S. Pat. application Ser. No. 919,901, in the name of J. S. Kieffer and Tony J. Wisneski, assigned to the assignee of the present application, entitled "Extrudable Composition for Forming Nonwoven Web or Pressure-Sensitive Elastomer Adhesive, and Use of Such Extrudable Composition in Forming Nonwoven Webs and Stretch-Bonded Laminates," the entire disclosure which is incorporated herein by reference and relied upon, discloses another such resiliently stretchable material. In this application, there is disclosed an extrudable composition for forming nonwoven elastomeric material having pressure-sensitive adhesive properties, nonwoven elastomeric sheet material, for example, fibrous nonwoven webs, formed of such composition, stretch-bonded laminates using such sheets and methods of forming such sheets in such laminates. The composition includes an elastomeric polymer and a tackifying resin, and can also include a polyolefin. The nonwoven sheet material can be a meltblown nonwoven web and the laminate can be formed by tensioning the elastomeric sheet material and bonding a gatherable web, for example, a spunbonded polypropylene web, to the tensioned sheet material by application of pressure, the bonding being accomplished due to the adhesivity of the elastomeric sheet material and without application of heat for softening the sheet material and/or gatherable web. The increased tackiness imparted to the elastomeric sheet by this internal tackifying agent resists in a composite web which resists delamination.

As used in the U.S. Pat. No. 4,657,802, and as contemplated herein, the term "nonwoven web" or "nonwoven layer" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web, elastomeric netting or a carded web of staple fibers.

It is to be clearly understood that the descriptions of methods for making a material suitable for outer cover 12 and the description of materials suitable for the outer cover 12 are exemplary only and not meant to be limiting.

The bodyside liner 34 may be airlaid, a bonded carded web, a powder-bonded carded web or a pattern bonded, spunbonded web of synthetic fibers such as polypropylene, polyester and the like.

Various materials are contemplated for use as the absorbent core 38, including fibrous materials, foams, particulates, etc. In general, the most economical liquid absorbent material for use in disposable diapers has been an absorbent fiber. The absorbent fiber most commonly used is cellulosic fiber such as comminuted wood pulp, commonly known in the art as "pulp fluff," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. Other softwood fluffs may be purchased from Kimberly-Clark Corporation, such as CR-54. Various hardwood fluffs may also be blended with the softwood fluffs to form the absorbent composite. A water-swellable hydrogel material, preferably in particulate form, may be used in a number of various arrangements within the absorbent composite in order to decrease the bulkiness and enhance the capacity of the composite 38. Many such hydrogel materials are known and available to those skilled in the art. It should be understood that additional elements could be provided in conjunction with those already set forth, without departing from the contemplated scope of the present invention and the description herein is not intended to be in any way limiting.

We claim:

1. A method of making a fixed fastener landing zone on an elastomeric surface of a garment, said method comprising the steps of:
   (a) providing an elastomeric nonwoven outer cover adapted for selected bodily registration;
   (b) providing said outer cover with front and rear waist panels resiliently stretchable in a direction essentially transverse to a longitudinal axis of said outer cover;
   (c) providing said outer cover with an intermediate crotch panel separating said waist panels from one another, with a pair of sides extending between and interconnecting said waist panels, delimiting a pair of elastically contractible leg openings along said sides of said crotch panel and delimiting a front and a rear longitudinally opposed pair of ears separated from one another by said crotch panel and comprising outermost lateral portions of said front and rear waist panels, respectively, wherein corresponding ones of said front and rear pairs of ears are engageable with one another to define an elastically contractible waist opening;
   (d) providing said rear pair of ears with elongated shapes presenting first surfaces superposable on second surfaces of said front pair of ears;
   (e) providing first fastening means on said first surfaces of said rear pair of ears;
   (f) forming inelastic landing zones on said second surfaces of said front ears and providing second fastening means on said landing zones that are releasably engageable with said first fastening means on said first surfaces of said rear ears, said inelastic landing zones tapering in dimension, in a decreasing manner, towards the longitudinal axis of said outer cover, whereby the formed inelastic landing zones selectively restrict the stretchability of said second surfaces and provide a tensile force distribution pattern across said front waist panel which directs tensile stresses away from said leg and waist openings while providing a band of abdominal support across said front waist panel between said landing zones when said outer cover is securely worn.

2. The method of claim 1 further comprising the steps of shaping said landing zones in generally triangular configurations and orienting said landing zones with respect to one another so that an area of highest tension is created in said band of abdominal support along a minimum distance between respective apexes of said landing zones that are equidistantly spaced on opposed sides of longitudinal axis.

3. The method of claim 1 further comprising the step of providing respective mechanical fastening means on said first and said second surfaces.

4. The method of claim 3 wherein said first and said second fastening means are hook and loop fasteners.

5. The method of claim 1 further comprising the step of forming a pattern of autogenous bonds surrounding said landing zones.

6. The method of claim 5 wherein the step of forming is by ultrasonically forming the pattern of bonds.

7. The method of claim 1 wherein the step of providing an elastomeric nonwoven outer cover further includes providing an elastomeric nonwoven outer cover that is resiliently stretchable from about 20 percent to about 200 percent.

8. The method of claim 1 wherein the step of providing an elastomeric nonwoven outer cover further includes providing an elastomeric nonwoven outer cover that is breathable.

9. The method of claim 1 wherein the step of providing an elastomeric nonwoven outer cover further includes forming said outer cover as a stretchbonded laminate by joining an elastic layer to at least one gatherable layer.

* * * * *